(12) United States Patent
Moonen et al.

(10) Patent No.: US 9,216,944 B2
(45) Date of Patent: Dec. 22, 2015

(54) PROCESS FOR THE PRODUCTION OF CHOLINE HYDROXIDE

(75) Inventors: Kristof Moonen, Hamme (BE); Dieter Ulrichts, Bruges (BE); Daan Scheldeman, Waregem (BE)

(73) Assignee: TAMINCO, Ghent (BE)

( * ) Notice: Subject to any disclaimer, the term of this patent is extended or adjusted under 35 U.S.C. 154(b) by 33 days.

(21) Appl. No.: 14/369,014

(22) PCT Filed: Dec. 29, 2011

(86) PCT No.: PCT/IB2011/003185
§ 371 (c)(1),
(2), (4) Date: Sep. 2, 2014

(87) PCT Pub. No.: WO2013/098575
PCT Pub. Date: Jul. 4, 2013

(65) Prior Publication Data
US 2015/0031917 A1   Jan. 29, 2015

(51) Int. Cl.
*C07C 213/00* (2006.01)
*C07C 215/00* (2006.01)
*C07C 217/00* (2006.01)
*C07C 213/10* (2006.01)
*C07C 213/04* (2006.01)

(52) U.S. Cl.
CPC ............ *C07C 213/10* (2013.01); *C07C 213/04* (2013.01)

(58) Field of Classification Search
CPC combination set(s) only.
See application file for complete search history.

(56) References Cited

U.S. PATENT DOCUMENTS

| 2,774,759 A | 12/1956 | Blackett et al. |
| 6,624,327 B1 * | 9/2003 | Blaufelder ............ C07C 227/02 562/526 |

FOREIGN PATENT DOCUMENTS

| DE | 241 596 A1 | 12/1986 |
| JP | 62-108848 A | 5/1987 |
| JP | 2002-317193 A | 10/2010 |

OTHER PUBLICATIONS

International Search Report for PCT/IB2011/003185 dated Sep. 14, 2012.

* cited by examiner

*Primary Examiner* — Clinton Brooks
(74) *Attorney, Agent, or Firm* — Sughrue Mion, PLLC

(57) ABSTRACT

A continuous process for the production of choline hydroxide includes reacting ethylene oxide, trimethylamine, and water in a reaction zone to form a reaction mixture and extracting heat from the reaction mixture. Subsequently, phase separation of the reaction mixture is induced to obtain a choline hydroxide phase and an organic liquid phase comprising trimethylamine. A choline hydroxide solution (e.g., at a concentration of about 40% to 50% by weight, based on total weight of the choline hydroxide solution) is obtained from the choline hydroxide phase.

18 Claims, No Drawings

PROCESS FOR THE PRODUCTION OF CHOLINE HYDROXIDE

CROSS REFERENCE TO RELATED APPLICATIONS

This application is a National Stage of International Application No. PCT/IB2011/003185, filed on Dec. 29, 2011, the contents of all of which are incorporated herein by reference in their entirety.

FIELD OF THE INVENTION

The invention relates to processes for the production of choline hydroxide solutions.

BACKGROUND OF THE INVENTION

Choline hydroxide or choline base (e.g., 2-(hydroxyethyl) trimethylammonium hydroxide), is a strong base which has applications in the production of other choline salts, for example, by neutralization with an appropriate acid or in applications where a strong base containing very low levels of inorganic ions is needed or can be tolerated. For instance, a choline base, such as choline hydroxide, is important in applications, such as in manufacturing electronics.

Choline hydroxide may be manufactured in a variety of different ways. For example, choline hydroxide may be produced from choline halides by displacing the halide counterion with hydroxide, for example, by using $Ag_2O$. Choline hydroxide may be formed by treating choline sulfate (which may be obtained by the reaction of dimethylamino ethanol and dimethyl sulfate) with $Ba(OH)_2$ resulting in $BaSO_4$ precipitate as coproduct.

Choline hydroxide may also be manufactured from choline halides. Choline halides (e.g., choline chloride) may be formed by the reaction of trimethylamine (TMA), ethylene oxide (EO), and HX, X being a halide, in one or more steps. Choline chloride may be converted to choline hydroxide by electrolysis in electrolytic cells having the cathode and anode separated by a cation exchange membrane (e.g., chloride ions are oxidized to $Cl_2$ at the anode and water is split into hydroxide ions and hydrogen gas at the cathode). Choline cations pass through the cation exchange membrane and combine with the hydroxide ions to form choline hydroxide. Regardless of the method used, producing choline hydroxide from choline halide results in a halogen containing side stream.

Choline hydroxide may also be produced by the direct reaction of trimethylamine (TMA), water and ethylene oxide (EO). The direct synthesis may be performed in a suitable solvent, e.g., water or water miscible alkanols. The direct method has the advantage of being much more atom efficient than the above described methods involving a choline halide starting material. However, the direct reaction of EO and TMA in the absence of a strong acid (e.g., HX) also has some disadvantages that are mainly due to the nature of the choline hydroxide product. Because of the strong basic nature of choline hydroxide, the molecule is prone to side product formation via O-ethoxylation and to color formation and degradation, for example, due to Hofmann elimination during synthesis.

As choline hydroxide has a similar base strength as NaOH, it is able to activate its own hydroxyl groups, resulting in an important competition between N and O-ethoxylation. In the case of N-ethoxylation a free amine (TMA) reacts with an ethylene oxide molecule, resulting in the desired choline molecule. In the case of O-ethoxylation, the hydroxyl group of a choline molecule reacts with another EO molecule resulting in choline like molecules with a higher degree of ethoxylation. O-ethoxylated products represent impurities in the final product. Furthermore, in many applications (e.g., production of various choline salts) the molarity of the hydroxide ion is important and therefore each molecule of EO spent on O-ethoxylation represents an economical loss. The degree of O-ethoxylated products that is observed during choline hydroxide synthesis may be dependent on the base strength of the solution, and hence upon the hydroxide (i.e., choline hydroxide) concentration. Indeed, the amount of O-ethoxylated products in a 10% aqueous reaction mixture is virtually zero, while in a commercial 45% choline hydroxide solution, the amount of higher choline ethoxylates can be as high as 10% by weight and higher. Apart from the concentration, O-ethoxylation is also enhanced by higher reactor temperatures.

Furthermore, choline hydroxide is known to be unstable and to develop color during synthesis and storage due to decomposition. Decomposition may occur via a so-called Hofmann elimination, resulting in the formation of TMA and acetaldehyde. Acetaldehyde ultimately leads to heavily colored condensation products, causing concentrated choline hydroxide solutions to become brown and black in a matter of a few days at room temperature. Hofmann elimination reactions are favored by higher temperature, and the temperature must be kept low during the synthesis of choline hydroxide in order not to obtain product already heavily colored immediately after preparation.

Thus, there remains a need for an effective and efficient process for producing choline hydroxide without undesired by-products and color formation.

SUMMARY OF THE INVENTION

Aspects of the present invention include processes for the production of choline hydroxide and the choline hydroxide solutions obtained therefrom. For example, the present invention relates to processes that allow for large scale, continuous production of concentrated aqueous choline hydroxide solutions in good quality under economically acceptable conditions. In particular, the process may include a single pass, continuous process for the synthesis of good quality choline hydroxide. The continuous reaction process may provide for the preparation of concentrated aqueous choline hydroxide solutions (e.g., about 40%-50%) at a temperature above about 50° C., with efficient and low cost heat control. In accordance with an embodiment of the invention, the O-ethoxylation products may also be kept at a level below 10%, below 5%, or below 1% (relative to choline hydroxide) in order to obtain economically advantaged consumption factors for ethylene oxide. Additionally, processes in accordance with the present invention may keep the color of freshly synthesized 40%-50% aqueous choline hydroxide solutions below, for example, about 200 APHA, while using a process temperature above 50° C.

According to one aspect of the invention, a continuous process for the production of choline hydroxide includes reacting ethylene oxide, trimethylamine, and water in a reaction zone to form a reaction mixture and extracting heat from the reaction mixture. Subsequently, a phase separation of the reaction mixture may be induced to obtain an aqueous choline hydroxide phase and an organic liquid phase comprising trimethylamine. A choline hydroxide solution may then be obtained from the aqueous phase. In one embodiment, the choline hydroxide solution comprises choline hydroxide at a concentration of about 40% to 50% by weight, based on total weight of the choline hydroxide solution.

According to another aspect of the invention, a continuous process for the production of choline hydroxide includes supplying ethylene oxide and water to a reaction zone with liquid trimethylamine to form a reaction mixture and passing the reaction mixture through a heat exchanger. Subsequently, the reaction mixture is passed to a zone where phase separation occurs to obtain a bottom layer comprising choline hydroxide and water and a top layer comprising trimethylamine. The choline hydroxide solution may then be obtained from the bottom layer.

Aspects of the present invention may also include a choline hydroxide solution that has a low APHA color value, e.g., of less than about 200 at room temperature and/or a stabilized choline hydroxide solution, for example, which includes a stabilizer, such as a dithionite salt and/or a dialkylhydroxylamine.

DETAILED DESCRIPTION OF THE INVENTION

Aspects of the present invention include single pass continuous processes for the production of choline hydroxide. As used herein, the terms "single pass" and "continuous" are intended to encompass processes that synthesize choline hydroxide in one or a single continuous process. In other words, the choline hydroxide does not require multiple steps (e.g., synthesizing an intermediate compound or compounds and, for example, in a separate operation, converting the intermediate(s) choline hydroxide). The process may be continuous in that the reactants may be introduced and products withdrawn simultaneously in an uninterrupted manner (e.g., the process does not require separate steps or batches).

As used herein and in the claims, the terms "comprising" and "including" are inclusive or open-ended and do not exclude additional unrecited elements, compositional components, or method steps. Accordingly, the terms "comprising" and "including" encompass the more restrictive terms "consisting essentially of" and "consisting of." Unless specified otherwise, all values provided herein include up to and including the endpoints given, and the values of the constituents or components of the compositions are expressed in weight percent or % by weight of each ingredient in the composition. Additionally, each compound used herein may be discussed interchangeably with respect to its chemical formula, chemical name, abbreviation, etc.

According to one embodiment of the invention, a continuous process for the production of choline hydroxide includes reacting ethylene oxide, trimethylamine, and water in a reaction zone to form a reaction mixture and extracting heat from the reaction mixture. Subsequently, a phase separation of the reaction mixture may be induced to obtain a choline hydroxide phase and an organic liquid phase comprising trimethylamine. A choline hydroxide solution may then be obtained from the choline hydroxide phase.

Choline hydroxide, also known as (2-hydroxyethyl) trimethyl-ammonium hydroxide, is an organic base suitable for many uses. For example, aqueous solutions of choline base are useful in connection with electronic applications, such as positive photoresist developing agents, stripping photoresists, anisotropic etching agents, and washing agents for silicon wafers.

Choline hydroxide may be produced by the direct reaction of ethylene oxide (EO), trimethylamine (TMA), water, which may be depicted as follows:

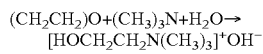

In a process according to the invention, the primary reactants, e.g., ethylene oxide, trimethylamine, and water, may be introduced into a reaction zone to form a reaction mixture. The primary reactants may be added as the starting materials individually or separately to the reaction zone, for example, in a continuous manner.

The reaction zone may include any suitable means or equipment known in the art to provide the proper reaction conditions. The reaction zone may include a continuous reactor where reactants are continuously fed into the reactor and emerge as a continuous stream of product. For example, the reaction zone may include a continuous reactor, such as a tubular reactor or plug flow reactor (e.g., a vessel through which flow is continuous, usually at steady state, and configured so that conversion of the chemicals and other dependent variables are functions of position within the reactor rather than of time.) Preferably, the reaction zone provides for some degree of turbulence as would be recognized by one of ordinary skill in the art. Suitable means known to one of ordinary skill in the art may also be used to enhance mixing (e.g., by piecing packing or other fillings in the tube). For example, the reactants may be pumped into a tubular reactor at a rate that creates turbulent flow and sufficient mixing of the reactants but at the same time is slow enough relative to the specific reactor configuration to ensure that the reaction temperature does not exceed an upper set point. The temperature may be monitored as a function of the distance along the reactor path for the purpose of controlling the rate of reactant(s) addition. In one embodiment of the present invention, the reaction zone is a continuous tubular reactor (CTR), which is vertically oriented. Other suitable reactors (e.g., continuous stirred tank reactor (CSTR)) known to one of ordinary skill in the art may also be employed.

Other reactants, solvents, catalysts, etc. may also be added with the primary reactants at the start of the reaction or during the reaction, for example, as will be appreciated by one of ordinary skill in the art. Additionally, any pre-treatments, such as pre-treating the water with trimethylamine may also be performed as needed (e.g., in the case where a stabilizer hydrolyzes at a neutral or acid pH).

The reaction occurs in a reaction medium. The reaction medium may include any suitable reaction medium or combination of mediums, e.g., water, trimethylamine, etc. The reaction medium may comprise an organic medium, which may include any solvent that is not miscible with water. In an exemplary embodiment, the reaction medium is excess trimethylamine (TMA). As used herein, the term "excess" is intended to mean a molar excess where the amount of TMA supplied is above the actual amount necessary for the formation of choline. In other words, the reaction medium comprises a molar excess of TMA (i.e., more TMA than is needed for the reaction to produce choline hydroxide). The excess TMA needs to be sufficient, however, to produce two phases. Without wishing to be bound to a particular theory, it is believed that by selecting an organic medium, such as TMA, as the reaction medium, phase separation may be induced to allow for easy extraction of the choline hydroxide under conditions suitable to produce the desired concentration of choline hydroxide and minimize by-products (e.g., O-ethyoxylation products and degradation reaction(s) leading to color formation).

It was discovered that the organic liquid (e.g., excess TMA) was found to act as an ideal medium to perform the choline hydroxide synthesis. When ethylene oxide was injected together with a sufficient amount of water into liquid TMA providing sufficient mixing, choline hydroxide was formed at a high reaction rate. Complete conversion of ethylene oxide may be observed at residence times in the reaction zone as low as 3 minutes. Longer residence times may also be used with no adverse effects. The use of a longer residence time may require the use of larger and more expensive equipment, however. The residence time in the reaction zone therefore preferably is between 1 and 1000 minutes, or more preferably between 5 and 100 minutes.

The reaction medium should be selected and provided in a suitable amount in order to provide for two phases (i.e., the organic phase and the choline hydroxide phase). The concentration of TMA in the choline hydroxide phase at which phase separation occurs may also depend on the concentration of choline hydroxide. According to one aspect of the present invention, the TMA:EO ratio in the reaction zone may be varied between about 2 and 500, about 5 and 200, or between about 10 and 50. Without wishing to be bound by theory, it is believe at lower TMA:EO ratios, more and more of the advantages of working in a TMA medium are lost, and high ratios are beneficial to the chemistry of the process, but require significantly larger equipment. The concentration of TMA in the aqueous choline base phase at which separation occurs may also depend on the choline base concentration. For example, the solubility of TMA may decrease with increasing amount of choline hydroxide.

The reactants and the reaction medium may be of any suitable state (e.g., liquid). In an exemplary embodiment, the entire process is run in the liquid phase. Thus, the reactants and reaction medium may be introduced in the liquid phase, the layers are in the liquid phase (e.g., liquid layers), and the products and by-products may be extracted in the liquid phase. For example, the ethylene oxide and water may be injected as liquids in a reaction zone with circulating liquid TMA as the reaction medium. A suitable reactor pressure may be applied in order to keep all reagents and products in the liquid phase. For example, the pressure may be between about 1 and 100 bar, or between about 2 and 50 bar. At 40° C., calculations suggest that all TMA will remain in the liquid phase at a pressure as low as 1.9 bar.

Because the reaction is exothermic, heat is extracted from the reaction mixture. The exothermic reaction enthalpy (heat of reaction) for the reaction of EO, TMA, and water to form choline hydroxide (117 kJ/mol EO) is sufficient to require careful thermal management. When water, TMA, and EO are mixed in the requisite proportions to obtain a 45% aqueous choline hydroxide solution, for example, the temperature will rise to about According to one aspect of the invention, the reaction may be occurring in a diluted form (e.g., in a TMA medium) and therefore the reaction heat liberated per mole of choline hydroxide formed is dissipated in a larger mass resulting in a limited temperature increase within an adiabatic reaction zone. For a ratio of TMA:EO=25, for example, the temperature of the reaction mixture will only increase about 23° C. A limited temperature increase may be handled by placing a heat exchanger in the reactor loop after the reaction zone, for example. Additionally, the degree of O-ethoxylation that is experienced in choline hydroxide synthesis processes is strongly dependent on the temperature, with higher temperatures increasing the amounts of undesirable side product(s). For example, so in a fed batch mode of operation, O-ethoxylation may become excessive towards the end of the reaction when the base concentration is the highest and the free amine concentration the lowest. Moreover, utilizing a large excess of trimethylamine increases the chance for an EO molecule to react with a free amine. Thus, maintaining the temperature minimizes the production of undesirable side product(s), such as ethoxylates.

The heat may be extracted and/or maintained at any suitable time before, during, or after the reaction. For example, the inlet temperature of the reactants, the temperature of the reaction mixture during the reaction, and the product and by-product streams may be maintained at a given temperature (e.g., above 50° C.). Without wishing to be bound by theory, by controlling the heat of the reaction mixture, an acceptable hydroxide content may be achieved and color formation may be minimized. Additionally, performing the TMA ethoxylation reaction in a TMA medium allows for the use of higher temperatures in the process. While processes described in the prior art typically work at low temperatures (e.g., below 50° C.) to reduce side product formation and degradation, the present invention allows for higher process temperatures while still providing choline hydroxide solutions with acceptably low levels of higher ethoxylates and low color. In one embodiment, the temperature throughout the process is maintained at a temperature in the range of about 40° C. to about 180° C., about 50° C. to about 150° C., about 50° C. to about 100° C., or about 50° C. to about 80° C.

The temperature increase over the reaction zone is dependent on the TMA:EO ratio used in the reaction zone. At a fixed production rate of choline hydroxide (and a fixed EO feed), the TMA:EO ratio may be increased by increasing the recycle rate of the organic top layer (e.g., TMA) that is recovered, while supplying an amount of fresh TMA that is in accordance with the amount of choline hydroxide formed and residual TMA that is withdrawn from the bottom of the system.

The temperature may be maintained using any suitable means known to one of ordinary skill in the art. For example, the heat may be controlled using a heat exchanger (e.g., parallel flow, counter flow, and cross flow). The heat exchanger may be part of the reaction zone, prior to, and/or subsequent to the reaction zone. For example, the temperature in the reaction zone may be controlled by passing a temperature controlling medium through the external mantle of the reaction vessel. By running at a process temperature above 40° C. or 50° C., for example, the reaction heat may be efficiently removed using readily available ambient cooling water. The collected product streams may also be cooled by passing the streams through a heat exchanger.

Once the reaction has occurred, a phase separation of the reaction mixture may be induced to obtain a choline hydroxide phase and an organic liquid phase comprising trimethyiamine. Although TMA and water are miscible liquids, it has been discovered that phase separation occurs when sufficiently high amounts of choline hydroxide are present in the aqueous phase. The phase separation provides a choline hydroxide phase or bottom layer and an organic liquid phase or top layer. The organic liquid phase or top layer comprises mostly TMA with a smaller amount of water and little or virtually no choline hydroxide. The choline hydroxide phase or bottom layer comprises choline hydroxide and water. Each of the phases also comprise minimal amounts of side products, for example, the O-ethoxylation products may be kept at a level below 10%, below 5%, below 2%, or below 1%.

Choline hydroxide, a highly polar compound, is not soluble in organic liquids, like TMA. The choline cation is strongly hygroscopic and strongly hydrated. In an exemplary embodiment, the reaction mixture is led to a zone with less turbulence than in the reaction zone (e.g., a zone with little to no turbulence, like a decanter) in which the aqueous choline hydroxide phase separates from the TMA rich medium. The aqueous choline hydroxide phase entrains significant amounts of water from the reaction medium, which results in an aqueous choline hydroxide lower layer at a concentration that is suitable for most applications (e.g., a concentration of about 40% to 50% by weight, based on total weight of the choline hydroxide solution). The aqueous choline hydroxide may be withdrawn from the bottom of the decanter and stripped of some excess TMA to yield commercial grade choline hydroxide material. Residual TMA is not desired in most w applications, as it imparts a strong fishy smell to the product. Thus, residual TMA may be removed by any of the techniques commonly known to those skilled in the art, such as stripping with an inert gas, boiling off under vacuum, distillation, and so forth. The concentration of choline hydroxide in the aqueous bottom layer may be controlled by the amount of water that is added together with EO in the reaction zone. In one embodiment of the present invention, the solutions of choline hydroxide have a concentration between about 40% and 50%.

Thus, in one aspect of the invention, the phase separation provides an organic liquid phase or rich top layer. The organic phase may comprise the organic liquid used for the reaction medium (e.g., trimethylamine). The TMA concentration may range from about 60 to 99%, about 75 to 95%, or about 80 to 90% in the top layer. The organic phase may also include water, negligible amounts of choline hydroxide, and negligible amounts of other by-products (e.g., ethoxylates). For example, the TMA rich top layer may contain about 5%-20% of water, dependent on the concentration of the bottom layer, along with low levels of choline hydroxide (e.g., below about 5%, below about 3%, or below about 1% choline hydroxide) and no other significant side products (e.g., below about 5%, below about 3%, or below about 1%), such as O-ethoxylates.

Because the organic phase may contain the organic liquid used for the reaction medium, the same organic liquid may be recycled to be used in the process again. In other words, the organic liquid may be separated from the organic phase and reintroduced into the reaction zone (e.g., recycled to an inlet of the reaction zone) to be further used as the reaction medium and/or as a reactant in the case of TMA. In other words, the TMA top layer may be advantageously recycled to the reaction zone as a reaction medium. In this way, the concentration of choline hydroxide in the reaction zone is so low that O-ethoxylation is significantly disfavored and the amount of higher ethoxylates found in the final solution withdrawn from the decanter bottom is significantly lower than what is typically obtained in single phase CSTR or fed batch process at high choline hydroxide concentrations.

The phase separation also provides a choline hydroxide liquid phase or bottom layer. The choline hydroxide may comprise choline hydroxide, water, and small amounts of the organic liquid used for the reaction medium (e.g., trimethylamine). For example, the choline hydroxide concentration may range from about 25 to 75%, about 30 to 60%, or about 40 to 50% in the bottom layer. The choline hydroxide may also include negligible amounts of other by-products (e.g., ethoxylates). For example, the bottom layer may contain about 5%-20% of water along with low levels of other significant side products (e.g., below about 5%, below about 3%, or below about 1%), such as O-ethoxylates.

In applications where choline hydroxide is used as a base, for instance in the neutralization of a variety of acids in order to obtain the corresponding choline salts, the concentration of hydroxide ions is an important quality parameter. Higher ethoxylates lead to a higher consumption of EO for the same number of hydroxide equivalents produced, and O-ethoxylation leads to a significant cost increase in the synthesis of choline hydroxide. Thus, aspects of the present invention result in both better quality choline hydroxide product and a significant reduction in raw material cost.

The phase separation may be induced using any suitable equipment and techniques known to one of ordinary skill in the art. In one embodiment, the phase separation occurs in a zone that has less turbulence than the reaction zone. In particular, an area having little to no turbulence may be preferred, which would be determined by one of ordinary skill in the art. For example, a decanter may be used with little or virtually no turbulence. Additional means known to one of ordinary skill in the art may also be used to enhance decantation in a decanter (e.g., by placing baffles). Decantation may be performed at the same temperature as the reactor inlet or slightly above. Performing decantation at a lower temperature may be performed without adverse effects, but low temperature decantation may require that the recycled top layer is heated again. It may be preferred that decantation is avoided in the reaction zone because it may be difficult to control in which phase the reaction is actually occurring. Additionally, there may be some buildup of the layers in the reaction zone.

The desired products and/or by products may be separated, extracted, or purified from the separate phases using any means and equipment known to one of ordinary skill in the art. For example, the products may be separated from each other using distillation, stripping with an inert gas, boiling off under vacuum, and so forth. For example, the choline hydroxide solution may be subsequently treated to remove some or all of the residual trimethylamine or O-ethoxylated side products.

The choline hydroxide solution may be obtained from the choline hydroxide phase. The choline hydroxide solution is preferably an aqueous choline solution, which includes a choline base and water. The preferred aqueous medium is water, and the water may be of any suitable type, e.g., distilled, deionized, treated, etc. Preferably, the water is in pure form with little to no impurities. The type and amount of aqueous medium is not especially limited, but may be recovered or employed in amounts sufficient to achieve a homogenous solution.

The choline hydroxide solution may comprise any suitable concentration of choline hydroxide. The concentration of choline hydroxide in the solution may be high (for example, on the order of about 30 to about 60 weight %, about 40 to about 50 weight % choline hydroxide, or about 45 weight % choline hydroxide) based on the total amount of the aqueous choline hydroxide solution. In one embodiment, the choline hydroxide solution comprises choline hydroxide at a concentration of about 40% to 50% by weight, based on total weight of the choline hydroxide solution.

The choline solution preferably is produced with a clear or slightly off-color (e.g., APHA of less than 500) appearance at room temperature (e.g., about 20-25° C.) under standard conditions. The color of the choline solution may be evaluated by measuring the American Public Health Association (APHA) color, for example, following appropriate American Society for Testing and Materials (ASTM) procedures (see e.g., ASTM D1209). APHA measurements may be obtained, for example, using a calibrated Lovibond PFX195 Tintometer with a 5 cm pathlength quartz cell. The APHA color value represents a scale ranging from a low, transparent/light to a high, opaque/dark sample. For example, a value less than 20 may be indicative of a clear or water-white sample, a value less than 100 is indicative of a clear or slightly off-color appearance sample, a value less than 500 is indicative of a clear to amber sample, and a value greater than 500 is indicative of amber to an opaque dark color. Thus, a lower value establishes a more clear/lighter sample whereas a higher value designates a more opaque/darker sample. As the darkness and opaqueness represents the presence of degradation reactions and associated by-products of the choline base, a lower value is desired. In one embodiment of the invention, the choline hydroxide solution has an APHA color value of 500 or less, 300 or less, 100 or less, 50 or less, or 20 or less when produced.

The choline hydroxide solution may also be stabilized using any suitable stabilizers known in the art, for example, for the purpose of preventing color formation and preserving the overall quality of the product. As used herein, the terms "stabilizing" and "stabilized" are intended to encompass a choline hydroxide solution that undergoes minimal or no degradation reactions that would otherwise deteriorate the quality of the choline hydroxide solutions. In other words, there is reduced or no development of heavy/dark color, formation of precipitates, volatility, a strong smell, etc. Instead, the stabilized choline solution may maintain a clear or slightly off-color (e.g., APHA of less than 500) appearance for an extended period of time (e.g., at least one week, at least one month, at least three months, etc.) at room temperature (e.g., about 20-25° C.) under standard conditions. Any suitable stabilizer may be used, including but are not limited to, dithionite salts (e.g., an alkali metal dithionite), amines (e.g., dialkylhydroxylamines), sulfites, hydroquinones, hydrides, carboxylic acids, piperazines, etc. For example, the stabilizer may comprise sodium dithionite, N,N-diethylhydroxylamine, ethylenediaminetetraacetic acid (EDTA), methoxyhydroquinone (MEHQ), tetramethylpiperazine-N-oxide (TEMPO), diethylenetriamine (DETA), benzaldehyde, sodium sulfite, boric add, tetraethylenetriamine (TETA), sodium borohydride, butylated hydroxyanisole, sodium metabisulfite, ascorbic acid, thiourea, and mixtures thereof. The stabilizer may be added in any suitable form (e.g., powder, aqueous, or in any form convenient for use in the process of choline hydroxide manufacture).

In one embodiment of the invention, a continuous process for the production of choline hydroxide includes supplying ethylene oxide and water to a reaction zone with liquid trimethylamine to form a reaction mixture and passing the reaction mixture through a heat exchanger. Subsequently, the reaction mixture is passed to a zone where phase separation occurs to obtain a bottom layer comprising choline hydroxide and water and a top layer comprising trimethylamine. The choline hydroxide solution may then be obtained from the bottom layer. Such a process allows for large scale, continuous production of concentrated aqueous choline hydroxide solutions in good quality under economically acceptable conditions. Additionally, the O-ethoxylation products may also be kept at a level below 10%, below 5%, below 2%, or below 1% (relative to choline hydroxide). Additionally, the color of freshly synthesized aqueous choline hydroxide solutions (e.g., 40%-50% concentrations) may be maintained below, for example, about 200 APHA while using a process temperature above 50° C.

EXAMPLES

Examples in accordance with the invention and comparative examples are described in more detail below.

Example 1

Showing Phase Separation Between Choline Hydroxide/Water and TMA

An aqueous solution of 45% choline hydroxide was thermostatted (60° C.) and stirred in a pressure resistant glass reactor. Liquid TMA was added to the liquid phase until two phases were clearly observed. When stirring was stopped, two clear layers were formed within one minute. The top and bottom layers were sampled and analyzed.

|  | Top Layer | Bottom Layer |
| --- | --- | --- |
| Choline Hydroxide | 0% | 43% |
| TMA | 89% | 2% |
| Water | 11% | 61% |

Comparative Example 1

Showing Increasing Competition of O-ethoxylation over N-Ethoxylation at Increasing Choline Hydroxide Concentrations in a Single Phase Fed Batch Reactor Water (4000 g) and TMA (1680 g) were loaded to a 20 liter batch stirred tank reactor (STR) reactor. EO (1416 g) was fed at such a rate that the EO in the gas cap did not exceed the concentration of 10V/V % (this typically takes about 4 to 6 hours). During the course of the fed batch reaction, the temperature was controlled between 35-40° C. Consecutive samples were taken over the reaction course and analyzed.

| EO fed (g) | Residual TMA (% w) | Choline Hydroxide (% w) | Higher Ethoxylates (% w) |
| --- | --- | --- | --- |
| 627 | 8.64 | 28.7 | 0.63 |
| 940 | 2.75 | 38.8 | 1.84 |
| 1128 | 1.13 | 42.7 | 3.40 |
| 1253 | 0.61 | 43.5 | 5.54 |
| 1316 | 0.38 | 43.0 | 7.33 |
| 1416 | 0.24 | 41.9 | 9.52 |

Example 2

Showing the Bottom Phase (Choline Hydroxide and Higher Ethoxylates) Obtained from a Tubular Reactor Ethylene oxide (5 g/h), water (34 g/h) and TMA (144 g/h) were fed to a double jacketed tubular reactor by means of mass flow controllers (molar ratio TMA:EO=21.5). The calculated residence time of the reactor was 10 minutes. The temperature of the tubular reactor was controlled by passing a heating medium through the external mantle. The liquid mixture was collected at the outlet of the reactor, cooled and stored in a pressure vessel. The complete system was kept under a pressure of 10 bar gauge by means of a back pressure valve. The bottom phase of the collecting vessel was sampled, stripped from residual TMA and analyzed.

| Temperature (° C.) | Choline Hydroxide (% w) | Higher Ethoxylates (% w) |
| --- | --- | --- |
| 50 | 43.3 | 2.3 |
| 60 | 41.9 | 4.3 |
| 70 | 41.2 | 5.2 |

Comparative Example 2

Occurrence of O-ethoxylation in Single Phase Mixed Reactor

An experiment was performed in the same experimental installation used in Example 2, but instead using a feed with a molar ratio TMA:EO=1.2 (32.5 g/h EO; 52.5 g/h TMA; 85.5 g/h water). Under these conditions, phase separation did not occur. Care was taken to keep the residence time the same as in Example 2. Reaction temperature was 50° C., pressure was 10 bar gauge, and excess TMA was removed from the product in the collecting vessel before sampling and analysis were performed. The final aqueous choline hydroxide solution was found to contain 40.1% choline hydroxide and 10.9% of higher ethoxylates.

Example 3

Shows the Effect of Even Higher Temperatures on Color of the Final Choline Hydroxide Solution An experiment was performed consistent with Example 2, but at a temperature up to 90° C. To be sure to keep all reagents in the liquid phase, the pressure of the system was controlled to 20 bar gauge. Residual TMA was stripped from the samples before further evaluation. The samples were stored in glass bottles under ambient conditions and color was assessed by visual inspection over time.

| Temperature (° C.) | Choline:higher ethoxylates mol/mol | Color Day 0 | Color Day 1 | Color Day 7 |
|---|---|---|---|---|
| 70 | 14.7:1 | Water clear | Pale yellow | Amber |
| 90 | 4.4:1 | Water clear | Pale yellow | Amber |

Comparative Example 3

Shows the Effect on Color of Choline Hydroxide made in Fed-Batch Mode

Some product obtained in Comparative Example 1 was stripped to remove residual TMA and was then stored in a glass bottle under ambient conditions and color was assessed by visual inspection over time.

| Color | | |
|---|---|---|
| Day 0 | Day 1 | Day 7 |
| Yellow | Amber | Dark |

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A continuous process for the production of choline hydroxide comprising:
   reacting ethylene oxide, trimethylamine, and water in a reaction zone to form a reaction mixture;
   extracting heat from the reaction mixture;
   subsequently, inducing phase separation of the reaction mixture to obtain a choline hydroxide phase and an organic liquid phase comprising trimethylamine; and
   obtaining a choline hydroxide solution from the choline hydroxide phase.

2. The process according to claim 1, wherein the reaction zone comprises an excess of the trimethylamine as a reaction medium.

3. The process according to claim 1, wherein the choline hydroxide solution is subsequently treated to remove residual trimethylamine or O-ethoxylated side products.

4. The process according to claim 1, wherein the organic liquid phase comprises less than 5% by weight of choline hydroxide.

5. The process according to claim 1, wherein the heat is extracted by passing the reaction mixture through a heat exchanger.

6. The process according to claim 1, wherein the phase separation occurs in a decanter.

7. The process according to claim 1, wherein the phase separation provides a top layer comprising liquid trimethylamine and a bottom layer comprising choline hydroxide and water.

8. The process according to claim 1, wherein the organic liquid phase is recycled to an inlet of the reaction zone.

9. The process according to claim 1, wherein the choline hydroxide solution comprises choline hydroxide at a concentration of about 40% to 50% by weight, based on total weight of the choline hydroxide solution.

10. The process according to claim 1, wherein the choline hydroxide solution comprises a stabilizer.

11. The process according to claim 10, wherein the choline hydroxide solution has an APHA color value of less than 200 at room temperature.

12. The process according to claim 1, wherein a residence time in the reaction zone is between about 1 and 1000 minutes.

13. The process according to claim 1, wherein the process occurs at temperatures between 40° C. to 150° C.

14. The process according to claim 1, wherein the process occurs at pressures between 1 bar and 100 bar.

15. The process according to claim 1, wherein the process occurs in liquid phase.

16. The process according to claim 1, wherein a ratio of trimethylamine to ethylene oxide, TMA:EO, is between about 2 and 500.

17. The process according to claim 1, wherein a ratio of trimethylamine to ethylene oxide, TMA:EO, is between about 10 and 50.

18. A continuous process for the production of choline hydroxide comprising:
   supplying ethylene oxide and water to a reaction zone with liquid trimethylamine to form a reaction mixture;
   passing the reaction mixture through a heat exchanger;
   subsequently, passing the reaction mixture to a zone where phase separation occurs to obtain a bottom layer comprising choline hydroxide and water and a top layer comprising trimethylamine; and
   obtaining a choline hydroxide solution from the bottom layer.

* * * * *